United States Patent [19]

Kagayama et al.

[11] Patent Number: 5,601,844
[45] Date of Patent: Feb. 11, 1997

[54] SUSTAINED RELEASE MEDICINAL PREPARATION

[75] Inventors: Akira Kagayama, Ikoma; Sumihisa Kimura, Kawanishi; Saburo Murata, Takarazuka; Sachiyo Tanimoto, Kadoma; Takehisa Hata, Nagaokakyo, all of Japan

[73] Assignee: Fujisawa Pharmaceutical Co., Ltd., Osaka, Japan

[21] Appl. No.: 424,498

[22] PCT Filed: Nov. 11, 1993

[86] PCT No.: PCT/JP93/01672

§ 371 Date: May 18, 1995

§ 102(e) Date: May 18, 1995

[87] PCT Pub. No.: WO94/10981

PCT Pub. Date: May 26, 1994

[30] Foreign Application Priority Data

Nov. 18, 1992 [JP] Japan .................. 4-308885

[51] Int. Cl.⁶ ............... A61K 9/16; A61K 9/50; A61K 9/48; A61K 31/44

[52] U.S. Cl. .............. 424/489; 424/45; 424/423; 424/426; 424/427; 424/436; 424/442; 424/451; 424/464; 514/291; 514/294

[58] Field of Search .................. 424/426, 489, 424/45, 423, 427, 436–442, 451, 464; 514/291, 294

[56] References Cited

U.S. PATENT DOCUMENTS

| | | | |
|---|---|---|---|
| 4,916,138 | 4/1990 | Ueda et al. | 514/294 |
| 5,196,437 | 3/1993 | Starzl et al. | 514/294 |
| 5,260,301 | 11/1993 | Nakanishi et al. | 514/291 |
| 5,368,865 | 11/1994 | Asakura et al. | 424/489 |
| 5,385,907 | 1/1995 | Asakura et al. | 514/291 |

FOREIGN PATENT DOCUMENTS

| | | |
|---|---|---|
| 0323042 | 7/1989 | European Pat. Off. |
| 0484936 | 5/1992 | European Pat. Off. |

OTHER PUBLICATIONS

Database WPI, Derwent Publications, AN 92–102775, and JP 4 49232, Feb. 18, 1992.

*Primary Examiner*—Carlos Azpuru
*Attorney, Agent, or Firm*—Oblon, Spivak, McClelland, Maier & Neustadt, P.C.

[57] ABSTRACT

A sustained release medicinal preparation is produced by enclosing a macrocyclic compound represented by 17-allyl-1,14-dihydroxy-12-[2-(4-hydroxy-3-methoxycyclohexyl)-1-methylvinyl)-23,25-dimethoxy-13,19,21,27-tetramethyl-11,28-dioxa-4-azatricyclo[22.3.1.0$^{4,9}$]octacos-18-ene-2,3,10,16-tetraone or 17-ethyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone, into the fine particles generally called microspheres which are made of biodegradable polymer. This preparation, when, for example, given by injection, appreciably improves the transference of said macrocyclic compound into the blood. Further, this is also used as an agent suitable for topical administration.

7 Claims, 1 Drawing Sheet

SUSTAINED RELEASE MEDICINAL PREPARATION

FIELD OF THE INVENTION

This invention relates to a sustained release medicinal preparation containing a macrocyclic compound or a pharmaceutically acceptable salt thereof shown by the general formula (I) presented hereinafter, which is attracting attention as a substance having a potent immunosuppressive activity, and more particularly, it relates to a sustained release medicinal preparation having said compound (I) or a salt thereof contained in a preparation in the form of so-called microspheres, and as a consequence applicable to various methods of administration including intramuscular injection and other injections, topical administration such as instillation into the eye, inhalation, intraarticular injection and the like, and further, oral administration and rectal administration.

PRIOR ART

A compound represented by the following general formula (I) and a pharmaceutically acceptable salt thereof has been known as a substance showing immunosuppressive activity (refer to Japanese Patent Laid-Open Sho 61(1986)-148181 and European Patent Laid-Open No. 0323042), for which application uses in various medical fields have been expected, including transplantation of organs such as heart, liver, kidney, bone marrow, skin, cornea, lung, pancreas, small intestine, muscle, nerve, limbs:

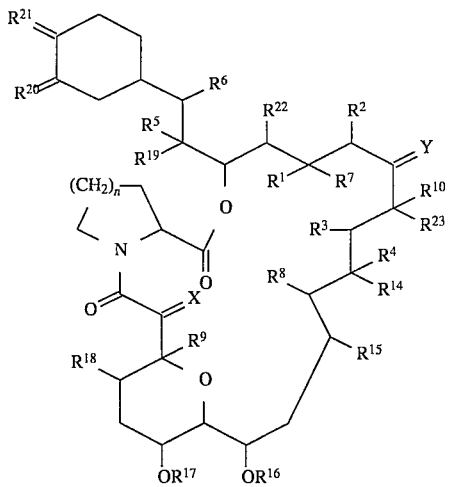

wherein each vicinal pair of $R^1$ and $R^2$, $R^3$ and $R^4$, $R^5$ and $R^6$ independently may a) represent two vicinal hydrogen atoms, or b) form a second bond between the vicinal carbon atoms to which they are attached;

in addition to the meanings above, $R^2$ may represent an alkyl group;

$R^7$ represents hydrogen, hydroxy group, protected hydroxy or alkyloxy group or, in conjunction with $R^1$ it may represent oxo group;

$R^8$ and $R^9$ independently represent hydrogen or hydroxy group;

$R^{10}$ represents hydrogen, alkyl group, alkyl group substituted by one or more hydroxy groups, alkenyl group, alkenyl group substituted by one or more hydroxy groups, or alkyl group substituted by oxo group;

X represents oxo group, (hydrogen atom, hydroxy group), (hydrogen atom, hydrogen atom) or —$CH_2O$—;

Y represents oxo group, (hydrogen atom, hydroxy group), (hydrogen atom, hydrogen atom) or N—$NR^{11}R^{12}$ or N—$OR^{13}$;

$R^{11}$ and $R^{12}$ independently represent hydrogen atom, or alkyl, aryl or tosyl group;

$R^{13}$, $R^{14}$, $R^{15}$, $R^{16}$, $R^{17}$, $R^{18}$, $R^{19}$, $R^{22}$ and $R^{23}$ independently represent hydrogen atom or alkyl group;

$R^{20}$ and $R^{21}$ independently represent oxo group, or they may independently represent ($R^{20}$a, hydrogen atom) and ($R^{21}$a, hydrogen atom) respectively; $R^{20}$a and $R^{21}$a independently represent hydroxy group, alkyloxy group, or $OCH_2OCH_2CH_2OCH_3$ or $R^{21}$a is protected hydroxy group;

in addition, $R^{20}$a and $R^{21}$a may together represent an oxygen atom in an epoxide ring;

n is 1, 2 or 3;

in addition to the meanings above, Y, $R^{10}$ and $R^{23}$, together with the carbon atoms to which they are attached, may represent a 5- or 6-membered N-, S- and/or O-containing heterocyclic ring, which may be saturated or unsaturated, and which may be substituted by one or more groups selected from alkyl group, hydroxy group, alkyl group substituted by one or more hydroxy groups, alkyloxy group, benzyl and —$CH_2Se(C_6H_5)$.

Such compound (I) and its pharmaceutically acceptable salt are prepared in the same manner as the one described in the above-mentioned two patent applications. Particularly, the macrolides, which are produced by fermentation of Streptomyces tsukubaensis No.9993 (FERM BP-927) or Streptomyces hygroscopicus subsp. yakushimaensis No.7238 (FERM BP-928), are numbered FR-900506, FR-900520, FR-900523 and FR-900525.

The compound (I) and a pharmaceutically acceptable salt thereof (hereinafter the term "compound (I)" is representatively used to show them) are expected, as described earlier, as a substance having immunosuppressive activity, and has been currently confirmed in various countries in the world of its effectiveness as an immunosuppressant for the rejection by organ transplantation. However, for inhibiting the rejection reaction after the operations it is necessary to administer the drug cautiously over a long period, and it has been desired to develop a dosage form excellent in a sustained release activity.

This invention has been started with an attention paid to the above-mentioned circumstances, and pursued with a view to provide a sustained release medicinal preparation which shows a long activity over a long period by achieving sustained release after being administered to a living body.

DISCLOSURE OF INVENTION

The sustained release medicinal preparation of this invention is produced by enclosing the active ingredient comprising the compound (I) into fine particles made of pharmaceutically acceptable biodegradable polymer.

Description will be given below in detail first of the various definitions used in the general formula (I) and their examples, and then their preferred embodiments.

The term "lower" as used in this specification means, unless otherwise indicated, a group having 1 to 6 carbon atoms.

Preferable examples of the "alkyl group" are a straight or branched chain aliphatic hydrocarbon residue, for example, a lower alkyl group such as methyl, ethyl, propyl, isopropyl, butyl, isobutyl, pentyl, neopentyl, hexyl and the like.

Preferable examples of the "alkenyl group" are a straight or branched chain aliphatic hydrocarbon residue having one double-bond, for example, lower alkenyl group such as vinyl, propenyl, butenyl, methylpropenyl, pentenyl, hexenyl and the like.

Preferable examples of the "aryl group" include, for example, phenyl, tolyl, xylyl, cumenyl, mesityl and naphthyl and the like.

Preferable protective groups in the "protected hydroxy group" are 1-(lower alkylthio)(lower) alkyl group such as a lower alkylthiomethyl group, for example, methylthiomethyl, ethylthiomethyl, propylthiomethyl, isopropylthiomethyl, butylthiomethyl, isobutylthiomethyl and hexylthiomethyl group, more preferably, $C_1$-$C_4$ alkylthiomethyl group, most preferably, methylthiomethyl group; trisubstituted silyl group such as a tri(lower)alkylsilyl, for example, trimethylsilyl, triethylsilyl, tributylsilyl and tert-butyl-dimethylsilyl and tri-tert-butylsilyl, or lower alkyldiarylsilyl, for example, methyldiphenylsilyl, ethyldiphenylsilyl, propyldiphenylsilyl and tert-butyl-diphenylsilyl, more preferably tri($C_1$-$C_4$) alkylsilyl group and $C_1$-$C_4$ alkyldiphenylsilyl group, most preferably, tert-butyl-dimethylsilyl group and tert-butyl-diphenylsilyl group; or an acyl group such as an aliphatic acyl, aromatic acyl or an aliphatic acyl substituted by an aromatic group, which are derived from a carboxylic acid, sulfonic acid and carbamic acid.

Examples of the aliphatic acyl are a lower alkanoyl group optionally having one or more suitable substituents such as carboxy, for example, formyl, acetyl, propionyl, butyryl, isobutyryl, valeryl, isovaleryl, pivaloyl, hexanoyl, carboxyacetyl, carboxypropionyl, carboxybutyryl and carboxyhexanoyl; a cyclo(lower)alkoxy(lower)alkanoyl group optionally having one or more suitable substituents such as lower alkyl, for example, cyclopropyloxyacetyl, cyclobutyloxyproplonyl, cycloheptyloxy-butyryl, menthyloxyacetyl, menthyloxyproplonyl, menthyloxy-butyryl, menthyloxypentanoyl and menthyloxyhexanoyl; camphorsulfonyl group or a lower alkylcarbamoyl group having one or more substituents such as carboxy or protected carboxy, for example, carboxy(lower)alkylcarbamoyl group, for example, carboxymethylcarbamoyl, carboxyethylcarbamoyl, carboxypropylcarbamoyl, carboxybutylcarbamoyl, carboxypentylcarbamoyl and carboxyhexylcarbamoyl, protected carboxy(lower)alkylcarbamoyl group such as tri(lower) alkylsilyl(lower)alkoxycarbonyl(lower)alkylcarbamoyl group, for example, trimethylsilylmethoxycarbonylethylcarbamoyl, trimethylsilylethoxycarbonylpropylcarbamoyl, triethylsilylethoxycarbonylpropylcarbamoyl, tertiary butyldimethylsilylethoxycarbonylpropylcarbamoyl and trimethylsilylpropoxycarbonylbutylcarbamoyl group and so on.

Examples of the aromatic acyl groups are an aroyl group optionally having one or more suitable substituents such as nitro, for example, benzoyl, toluoyl, xyloyl, naphthoyl, nitrobenzoyl, dinitrobenzoyl and nitronaphthoyl; or an arenesulfonyl group optionally having suitable substituents such as halogen, for example, benzenesulfonyl, toluenesulfonyl, xylenesulfonyl, naphthalenesulfonyl, fluoro-benzenesulfonyl, chlorobenzenesulfonyl, bromobenzenesulfonyl and iodobenzenesulfonyl.

Examples of the aliphatic acyl groups substituted by aromatic group include ar(lower)alkanoyl group optionally having one or more substituents such as lower alkoxy or trihalo(lower)alkyl, for example, phenylacetyl, phenylpropionyl, phenylbutyryl, 2-trifluoromethyl-2-methoxy-2-phenylacetyl, 2-ethyl-2-trifuluoromethyl-2-phenylacetyl and 2-trifluoromethyl-2-propoxy-2-phenylacetyl.

More preferable acyl groups among the aforesaid acyl groups are $C_1$-$C_4$ alkanoyl group optionally having carboxy, cyclo($C_5$-$C_6$)alkyloxy($C_1$-$C_4$)alkanoyl group having two ($C_1C_4$)alkyl at the cycloalkyl group, camphorsulfonyl group, carboxy($C_1$-$C_4$)alkylcarbamoyl group, tri($C_1$-$C_4$)alkylsilyl($C_1$-$C_4$)alkoxycarbonyl($C_1$-$C_4$)alkylcarbamoyl group, benzoyl group optionally having one or two nitro groups, benzenesulfonyl group having halogen or phenyl($C_1$-$C_4$)alkanoyl group having $C_1$-$C_4$ alkoxy and trihalo($C_1$-$C_4$)alkyl group. Among these, the most preferable ones are, for example, acetyl, carboxyproplonyl, menthyloxyacetyl, camphorsulfonyl, benzoyl, nitrobenzoyl, dinitrobenzoyl, iodobenzenesulfonyl and 2-trifluoromethyl-2-methoxy-2-phenylacctyl.

Preferable examples of the "heterocyclic groups in the 5- or 6-membered nitrogen, sulfur and/or oxygen containing ring" include a pyrrolyl group or a tetrahydrofuryl group.

The pharmaceutically acceptable salts of the compound (I) include conventional non-toxic and pharmaceutically acceptable salts such as the salts with inorganic or organic bases, for example, an alkali methal salt such as sodium salt or potassium salt, an alkali earth metal salt such as calcium salt or magnesium salt, an ammonium salt or an amine salt such as triethylamine salt or N-benzyl-N-methylamine salt.

With regard to the compound (I) of the present invention, there may be one or more conformer(s) or stereoisometic pairs such as optical isomers and geometrical isomers due to the presence of asymmetric carbon atom(s) and double bond(s), and such isomers are also included within a scope of the present invention.

Best Mode of Practicing the Invention

The fine particles made of biodegradable polymer to be used in the present invention is generally called microspheres, and the microspheres themselves belong to a technique known to public.

However, the technique of enclosing the compound (1) of the present invention which belongs to a macrocyclic compound, into microspheres remains unknown up to now, and it has been completely unknown whether the compound (I) having such a macrocyclic ring, when being enclosed into microspheres, can be made a medicinal preparation without notable difficulties, or, even if it is successfully made a medicinal preparation, whether it can be endowed with excellent sustained release activity.

It was found, however, that the preparation derived by using a biodegradable polymer represented by polylactic acid (referred to as PLA hereinafter) or lactic acid-glycolic acid copolymer (referred to as PLGA hereinafter) as a constituent of the microspheres and by dispersing the compound (I) in those fine particles, allows the compound (I) to release gradually in a very stable manner.

For the biodegradable polymer to be used in the present invention, in addition to the above PLA and PLGA, polyglycolic acid, polyalkyl α-cyanoacrylate, poly ε-caprolacton, polyamino acid, polyhydroxy butyric acid, polyhydroxy valeric acid, polyhydroxy butyric acid-hydroxy valeric acid copolymer can be cited as suitable examples.

The amount of the compound (I) to be contained in the fine particles made of the biodegradable polymer should be determined according to the administration purposes in relation to humans or animals and to the administration routes (sites), but, it is recommended to choose 0.01–50 weight %, or more preferably 0.1–20 weight %.

The size of the fine particles used in this invention is not confined to a certain range worthy of note and, in short, it is only necessary for them to have a size capable of passing through an injection needle, and it is preferably 200 μm or less.

The method of producing the fine particles of the present invention is not confined to a specific one, but a representative method is presented here just as an illustration. A biodegradable polymer is dissolved in an organic solvent such as methylene chloride, acetonitril, dioxane or the like, and the compound (I) is dissolved in that solution. Thereafter, to the resultant solution is added a medium for precipitation to precipitate fine particles. The resultant solution containing the particles is emulsified, and the particles are separated and freeze-dried. These fine particles contain the compound (I). It was found that their size tends to be smaller as the organic solvent is added more, and to be greater as the organic solvent is added less. The added amount of the organic solvent should be 1–50 times(v/w) the amount of the biodegradable polymer, or more preferably 1–10 times.

On the other hand, as the medium for precipitation, a hydrophilic solvent is preferable such as gelatin aqueous solution, polyvinyl alcohol, lower alcohols (methanol, ethanol, etc.) and ketones (acetone, etc.), and there is a tendency wherein the size of the fine particles becomes smaller when the crystallization medium, after being added, is highly concentrated in the system, and greater when it is thinly concentrated in the system. The added amount of the medium for precipitation should be 0.1–10 weight % in terms of the concentration after addition, and more preferably 0.25–2 weight %.

The fine particles thus provided should be administered after being dispersed into a dispersion medium appropriate to a given administration route, and, as an example, when they are used for topical application such as intraarticular injection, they are dispersed in distilled water for injection or in physiological saline. It is possible to add a variety of pharmaceutically acceptable additives into the fine particles of the present invention or the drug for injection or for oral use which are prepared by dispersing the particles into the said dispersion medium. For such additives, surfactants, disintegrators, tonicity balancers, analgesics, excipients, thickners, stabilizers, antiseptics and the like can be cited.

The medicinal preparation of the present invention can also be used effectively when the compounds disclosed in the documents listed below are employed as active ingredients, such as EP-A-353678, Japanese Patent Laid-Open No. HEI 2(1990)-74330, PCT/GB90/01262, EP-A-413532, PCT/JP91/00314, British Patent Application No. 9012963.6, British Patent Application No. 9014136.7, British Patent Application No. 9014681.2, British Patent Application No. 9014880.0, British Patent Application 9014881.8, British Patent Application No. 9015098.8, British Patent Application No. 9016115.9, British Patent Application No. 9016693.5, EP-A-323865, EP-A-349061, EP-A-358508, EP-A-364031, EP-A-364032, EP-A-378317, EP-A-378320, EP-A-378321, EP-A-388153, EP-A-396399, EP-A-396400, EP-A-399579, EP-A-403242, EP-A-428365, EP-A-356399, GB 2225576.A, EP-A-402931 and EP-A-427680.

In addition, use of cyclosporins or rapamycins can also allow the production of the sustained release medicinal preparation of the present invention.

DESCRIPTION OF PREFERRED EMBODIMENTS

Figure 1:
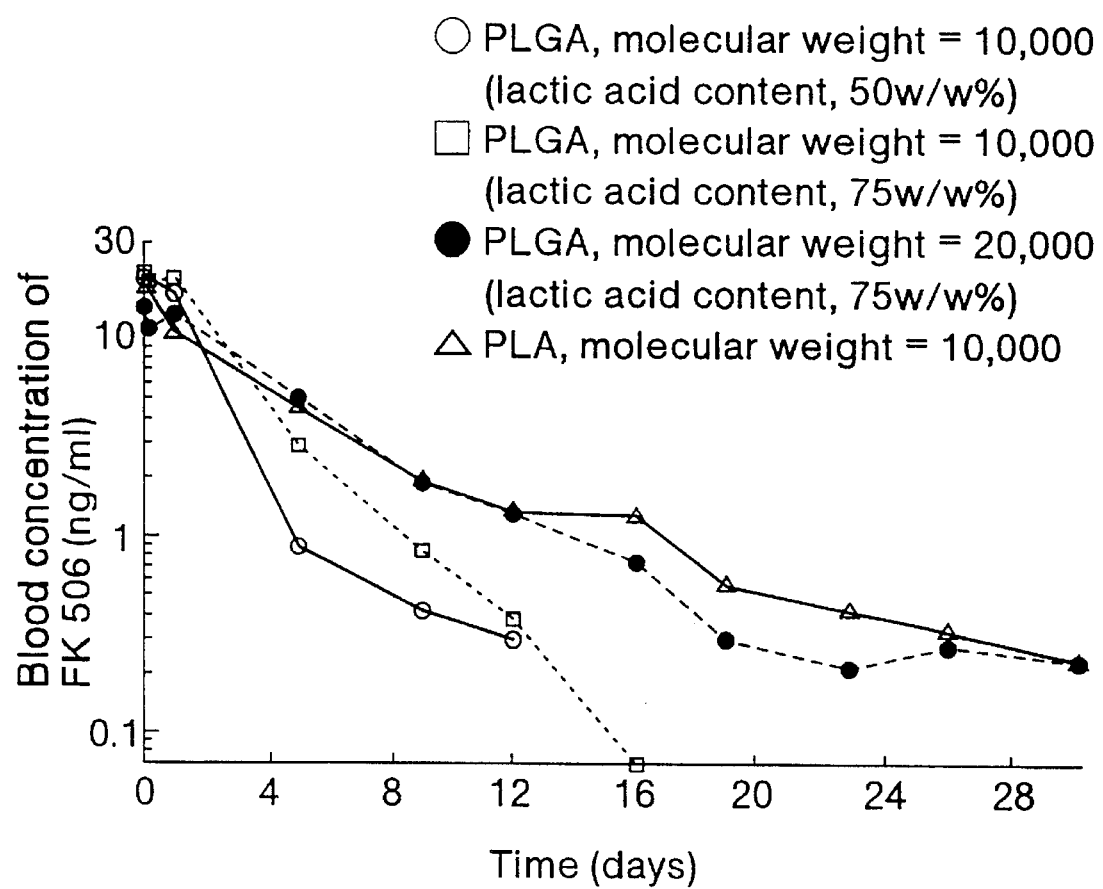
FIG. 1 is a graph showing the concentration of FK506 in blood over time using various microsphere vehicles.

Demonstrative description will be given below of the present invention using preferred embodiments, but the present invention should not be confined to these embodiments.

As the compound (I), the following compound in which:
$R^1$, $R^2$, $R^8$, $R^{23}$=hydrogen
$R^7$, $R^9$=hydroxy group
$R^{10}$=allyl group
$R^{14}$, $R^{15}$, $R^{16}$, $R^{17}$, $R^{18}$, $R^{19}$, $R^{22}$=methyl group
$R^{20}$=($R^{20}$a, H) ($R^{20}$a=methoxy group)
$R^{21}$=($R^{21}$a, H) ($R^{21}$a=hydroxy group)
X, Y=oxo group n=2
$R^3$, $R^4$=form a second bond between the vicinal carbon atoms to which they are attached,
$R^5$, $R^6$=form a second bond between the vicinal carbon atoms to which they are attached, being in a free form was used. The compound has an excellent immunosuppressive activity and is referred to hereinafter as FK506.

Production of Fine Particles

FK506 (0.05 g), methylene chloride (2 ml, 4 ml, 8 ml) and PLGA (0.5 g) are mixed to give a homogeneous solution, to which is added 1% gelatin aqueous solution (200 ml) to precipitate fine particles. They are placed in a homomixer and emulsified at 6° C.×5000 rpm×5 min. By passing nitrogen gas through this emulsified solution the solvent is removed by distillation, and the residue, after being filtered through a 100 μm mesh, is submitted to centrifugation at 2500 rpm×5 min. The precipitate is, after being washed with water, submitted again to centrifugation, and, after being dispersed again in water, freeze-dried. The size of the fine particles thus produced is as follows:

37.3 μm when 2 ml methylene chloride is used;

16.1 μm when 4 ml methylene chloride is used; and 7.5 μm when 8 ml methylene chloride is used.

Change of the Concentration in Blood

Using the particles having a diameter of 16.1 μm from among those fine particles derived in the manner described above, intraarticular injection was tried on rats at a rate of 2 mg/kg. The change of FK506 concentration in a whole blood is shown in FIG. 1.

As seen from the FIG. 1 (the ordinate is logarithmic scale), it is understood that the sustained release of FK506 occurs over a very long period, and thus the estimation that this is an excellent sustained release medicinal preparation is established.

Effects of the Invention

The present invention, having the above-described structure, allows the compounds (I) having a macrocycle including FK506 to act as stable fine particles, which show stable sustained release over a very long period, when administered to humans or animals. They can also be served as agents suitable for topical application, so a larger amount of the compounds (I) than that for the parenteral administration can be administered without causing any apprehension for its systemic toxicity.

The medicinal preparation of this invention is used as dispersed preparation, by adding, whenever needed, a dispersion medium thereto, so it is excellent in storage stability, and it was further confirmed that this preparation, even when getting contact with body fluids, does not allow crystallization of the active ingredients, thus achieving excellent bioavailability. Further, the other advantages of this medicinal preparation is to be easily administered to children, and to easily adjust their dose.

Industrial Field of Utilization

The pharmaceutical formulation according to the present invention, due to the pharmacological activities of the tricyclo compound (I), is useful for the treatment and prevention of immune-mediated diseases such as rejection in transplantation of organs or tissues such as heart, kidney, liver, bone marrow, skin, cornea, lung, pancreas, small intestine, limbs, muscle, nerve, intervertebral disk, trachea, etc.; graft-versus-host reaction to bone marrow transplantation; autoimmune disease such as rheumatoid arthritis, systemic lupus erythematosus, Hashimoto's thyroidiris, multiple sclerosis, myasthenia gravis, type I diabetes, and the like; and further infectious diseases caused by pathogenic microorganisms (for example, *Aspergillus fumigatus, Fusarium oxysporma, Tricophyton asteroides*, etc.).

Further, the preparation of the tricyclo compounds (I) are also useful for the treatment and the prophylaxis of inflammatory and hyperproliferative skin diseases and cutaneous manifestations of immunologically-mediated illnesses, such as psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitides, erythemas, cutaneous eosinophilias, lupus erythematosus, acne and alopecia arcata;

various eye diseases such as autoimmune diseases and so on (e.g. keratoconjunctivitis, vernal conjunctivitis, uveitis associated with Behcet's disease, keratitis, herpetic keratitis, conical keratitis, dystrophia epithelialis corneae, corneal leukoma, ocular pemphigus, Mooren's ulcer, seleritis, Graves' ophthalmopathy, Vogt-Koyanagi-Harada syndrome, sarcoidosis, etc.);

reversible obstructive airways disease, which includes conditions such as asthma (e.g. bronchial asthma, allergic asthma, intrinsic asthma, extrinsic asthma and dust asthma), particularly chronic or inverterate asthma (e.g. late asthma and airway hyper-responsiveness), bronchitis and the like;

inflammation of mucosa and blood vessels such as gastric ulcers, vascular injury caused by ischemic diseases and thrombosis, ischemic bowel disease, enteritis, necrotizing enterocolitis, intestinal lesions associated with thermal burns, leukotriene $B_4$-mediated diseases;

intestinal inflammation/allergies such as coeliac disease, proctitis, eosinophilic gastroenteritis, mastocytosis, Crohn's disease and ulcerative colitis;

food related allergic diseases which have symptomatic manifestation remote from the gastro-intestinal tract, for example, migraine, rhinitis and eczema;

renal diseases such as interstitial nephritis, Goodpasture's syndrome, hemolytic-uremic syndrome and diabetic nephropathy;

nervous diseases such as multiple myositis, Guillain-Barre syndrome, Meniere's disease, polyneuritis, mononeuritis, and radiculopathy;

endocrine diseases such as hyperthyroidism and Basedow's disease;

hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia;

bone diseases such as osteoporosis;

respiratory diseases such as sarcoidosis, pulmonary fibrosis, and idiopathic interstitial pneumonia;

skin diseases such as dermatomyositis, leukoderma vulgaris, ichthyosis vulgaris, photoallergic sensitivity and cutaneous T cell lymphoma;

circulatory diseases such as arteriosclerosis, atherosclerosis, aortitis syndrome, polyarteritis nodosa and myocardosis;

collagen diseases such as scleroderma, Wegener's granuloma and Sjöegren's syndrome;

adiposis;

eosinophilic fasciitis;

periodontal disease such as lesion of gingiva, periodontium, alveolar bone, substantia ossea dentis;

nephrotic syndrome such as glomerulonephritis; male pattern alopecia or alopecia senilis;

muscular dystrophy;

pyoderma and Sezary's syndrome;

Addison disease;

active oxygen-mediated diseases, for example, organ injury such as ischemia-reperfusion injury of organs (e.g. heart, liver, kidney, digestive tract) which occurs on preservation, transplantation or ischemic diseases (e.g. thrombosis, cardiac infarction): intestinal diseases such as endotoxin-shock, pseudomembranous colitis, colitis caused by drug or radiation: renal diseases such as ischemic acute renal insufficiency, chronic renal insufficiency: pulmonary diseases such as toxicosis caused by lung-oxygen or drug (e.g. paracort, bleomycins), lung cancer, pulmonary emphysema: ocular diseases such as cataracta, siderosis, retinitis, pigmentosa, senile macular degeneration, vitreous scarring, corneal alkali burn: dermatitis such as erythema multiforme, linear IgA bullous dermatitis, cement dermatitis: and others such as gingivitis, periodontitis, sepsis, pancreatitis, diseases caused by environmental pollution (e.g. air pollution), aging, carcinogens, metastasis of carcinoma, hypobaropathy;

diseases caused by histamine or leukotriene $C_4$ release;

Behcet's disease (e.g. intestinal type, vascular type, nervous type, oral cavity, skin, eye, external genitalia, joint, epididymis, lung, kidney, etc.) and the like.

And further, the preparation of the tricyclo compounds (I) have liver regenerating activity and/or activities of stimulating hypertrophy and hyperplasia of hepatocytes. Therefore, they are useful for the treatment and prevention of hepatic diseases such as immunogenic diseases (e.g. chronic autoimmune liver diseases such as the group consisting of autoimmune hepatic disease, primary biliary cirrhosis and sclerosing cholangitis), partial liver resection, acute liver necrosis (e.g. necrosis caused by toxins, viral hepatitis, shock or anoxia), hepatitis B, hepatitis non-A/non-B, cirrhosis and hepatic failure such as fulminant hepatitis, late-onset hepatitis and "acute-on-chronic" liver failure (acute liver failure on chronic liver diseases).

And further, the preparation of the tricyclo compounds (I) are useful for various diseases because of their useful pharmacological activity such as augmenting activity of chemotherapeutic effect, preventing or treating activity of cytomegalovirus or AIDS virus infection, anti-neoplasmic activity, anti-inflammatory activity, and so on.

What is claimed is:

1. A sustained release medicinal preparation characterized by enclosing a tricyclo compound of the following general formula (I) or a pharmaceutically acceptable salt thereof in fine microspheres made of a pharmaceutically acceptable biodegradable polymer selected from the group consisting of polylactic acid, copolymer of lactic acid and glycolic acid, and mixtures thereof,

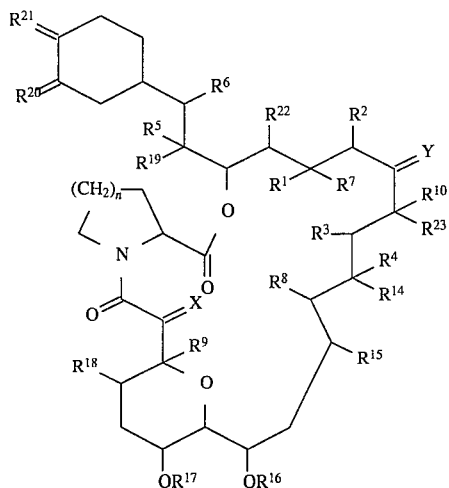

(I)

wherein each vicinal pair of $R^1$ and $R^2$, $R^3$ and $R^4$, $R^5$ and $R^6$ independently may, a) represent two vicinal hydrogen atoms, or b) form a second bond between the vicinal carbon atoms to which they are attached;

in addition to the meanings above, $R^2$ may represent an alkyl group;

$R^7$ represents hydrogen, hydroxy group, protected hydroxy or alkyloxy group or, in conjunction with $R^1$, it may represent oxo group;

$R^8$ and $R^9$ independently represent hydrogen or hydroxy group; $R^{10}$ represents hydrogen, alkyl group, alkyl group substituted by one or more hydroxy groups, alkenyl group, alkenyl group substituted by one or more hydroxy groups, or alkyl group substituted by oxo group;

X represents oxo group, (hydrogen atom, hydroxy group), (hydrogen atom, hydrogen atom) or —$CH_2O$—;

Y represents oxo group, (hydrogen atom, hydroxy group), (hydrogen atom, hydrogen atom) or N—$NR^{11}R^{12}$ or N—$OR^{13}$;

$R^{11}$ and $R^{12}$ independently represent hydrogen atom, or alkyl, aryl or tosyl group;

$R^{13}$, $R^{14}$, $R^{15}$, $R^{16}$, $R^{17}$, $R^{18}$, $R^{19}$, $R^{22}$ and $R^{23}$ independently represent hydrogen atom or alkyl group;

$R^{20}$ and $R^{21}$ independently represent oxo group, or they may independently represent ($R^{20}{}_a$, hydrogen atom) and ($R^{21}{}_a$, hydrogen atom) respectively; $R^{20}{}_a$ and $R^{21}{}_a$ independently represent hydroxy group, alkyloxy group, or $OCH_2OCH_2CH_2OCH_3$ or $R^{21}{}_a$ is protected hydroxy group;

in addition, $R^{20}{}_a$ and $R^{21}{}_a$ may together represent an oxygen atom in an epoxide ring;

n is 1, 2 or 3;

in addition to the meanings above, Y, $R^{10}$ and $R^{23}$, together with the carbon atoms to which they are attached, may represent a 5- or 6-membered N-, S- and/or O-containing heterocyclic ring, which may be saturated or unsaturated, and which may be substituted by one or more groups selected from alkyl group, hydroxy group, alkyl group substituted by one or more hydroxy groups, alkyloxy group, benzyl and —$CH_2Se(C_6H_5)$.

2. The sustained release medicinal preparation of claim 1 wherein the tricyclic compound is a compound of the formula (I), in which $R^3$ and $R^4$, $R^5$ and $R^6$ may form a second bond between carbon atoms to which they are attached, $R^8$ and $R^{23}$ independently represent hydrogen atom, $R^9$ represents hydroxy group, $R^{10}$ represents methyl, ethyl, propyl or allyl group, X represents (hydrogen atom, hydrogen atom) or oxo group, Y represents oxo group, each of $R^{14}$, $R^{15}$, $R^{16}$, $R^{17}$, $R^{18}$, $R^{19}$ and $R^{22}$ represents methyl group, $R^{20}$ and $R^{21}$ independently represent ($R^{20}a$, hydrogen atom) or ($R^{21}a$, hydrogen atom) (in which $R^{20}a$ and $R^{21}a$ represent respectively hydroxy or alkyloxy group, or $R^{21}a$ represents a protected hydroxy group) and n is 1 or 2.

3. The sustained release medicinal preparation of claim 1 wherein the tricyclic compound has the formula (I), in which $R^7$ represents hydrogen atom, hydroxy group or protected hydroxy group, X represents oxo group, $R^{20}a$ represents methoxy group, $R^{21}a$ represents hydroxy group or protected hydroxy group.

4. The sustained release medicinal preparation as defined in claim 3 wherein the tricyclic compound (I) is 17-allyl-1, 14-dihydroxy-12-[2-(4-hydroxy-3-methoxy-cyclohexyl)-1-methylvinyl)-23,25-dimethoxy-13,19,21,27-tetramethyl-11, 28-dioxa-4-azatricyclo[22.3.1.0$^{4,9}$]octacos-18-ene-2,3,10, 16-tetraone.

5. The sustained release medicinal preparation as defined in claim 1 wherein the content of the tricyclo compound (I) is 0.01–50 weight %.

6. The sustained release medicinal preparation of claim 5, in which the size of the fine microspheres is 200 μm or less.

7. The sustained release medicinal preparation of claim 6, which is adapted for intraarticular injection.

* * * * *